United States Patent [19]

Sawamura et al.

[11] 4,284,897
[45] Aug. 18, 1981

[54] FLUORESCENCE DETERMINING MICROSCOPE UTILIZING LASER LIGHT

[75] Inventors: Ichiro Sawamura; Mamoru Aihara; Kazuhiko Nakamura; Youichi Kondo, all of Hachioji, Japan

[73] Assignee: Olympus Optical Company Ltd., Tokyo, Japan

[21] Appl. No.: 885,640

[22] Filed: Mar. 13, 1978

[30] Foreign Application Priority Data

Apr. 30, 1977 [JP] Japan .................................. 52-50558

[51] Int. Cl.³ .......................................... G01N 21/64
[52] U.S. Cl. ............................................... 250/461 B
[58] Field of Search ....................... 250/461 R, 461 B; 356/39

[56] References Cited

U.S. PATENT DOCUMENTS

| | | | |
|---|---|---|---|
| 3,657,537 | 4/1972 | Wheeless, Jr. et al. | 250/461 B |
| 3,950,649 | 4/1976 | Yonekubo | 250/461 B |
| 4,058,732 | 11/1977 | Wieder | 250/461 B |
| 4,172,227 | 10/1979 | Tyrer et al. | 250/461 B |

Primary Examiner—Alfred E. Smith
Assistant Examiner—Janice A. Howell
Attorney, Agent, or Firm—Weinstein & Sutton

[57] ABSTRACT

A fluorescence determining microscope scans the surface of a specimen with laser light. The fluorescence produced is split into components of different wavelengths, and the fluorescence of the respective wavelengths is determined.

5 Claims, 4 Drawing Figures

FIG. 1
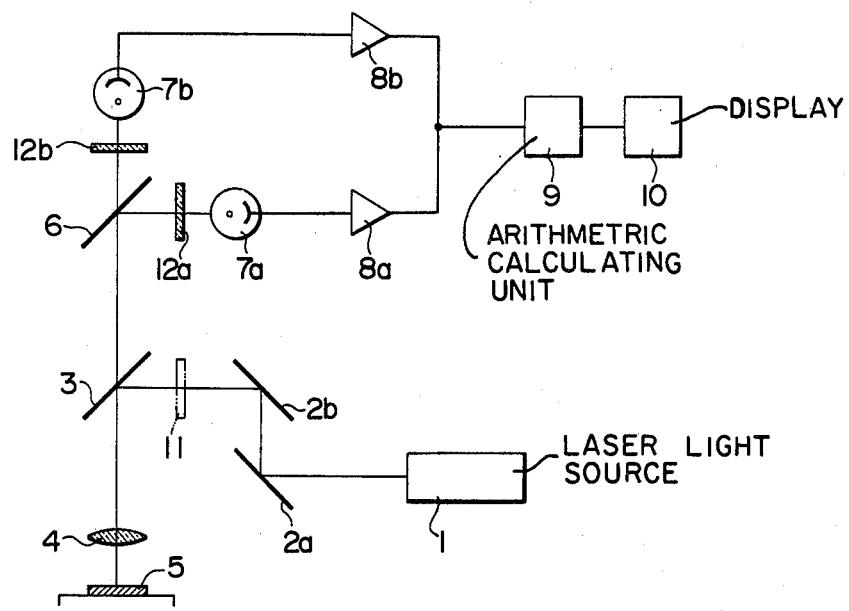
FIG. 2
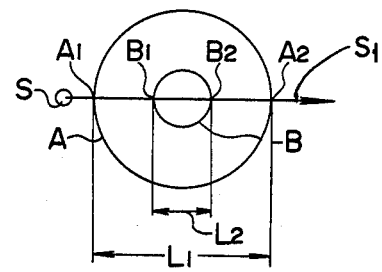
FIG. 3(a)  FIG. 3(b)
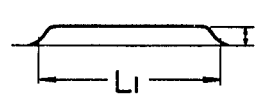 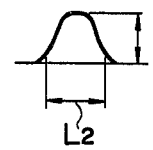

FLUORESCENCE DETERMINING MICROSCOPE UTILIZING LASER LIGHT

BACKGROUND OF THE INVENTION

In the prior art practice of determining whether cells under examination are affected by cancer, the cells have been observed under a microscope, and an overall determination has been rendered based upon the size and the shape of cells and nuclei. Such determination is devoid of objective standards, and is only possible by an experienced expert.

SUMMARY OF THE INVENTION

The invention is based on the finding that the fluorescence produced by the cytoplasm is of a wavelength which is different from that of the fluorescence produced by the nucleus. Therefore, it is an object of the invention to provide a fluorescence determining microscope utilizing laser light which scans a cell with laser light and which splits the resulting fluorescence into components of different wavelengths, which are subjected to a photometry to provide an objective determination as to whether the cell is affected by cancer, in a simple manner.

BRIEF DESCRIPTION OF THE DRAWINGS

FIG. 1 is a schematic layout of the fluorescence determining microscope of the invention;

FIG. 2 is a diagrammatical view illustrating the manner of scanning a cell; and

FIGS. 3a and b graphically show the amount of fluorescence produced during the scanning process illustrated in FIG. 2.

DESCRIPTION OF PREFERRED EMBODIMENT

Referring to FIG. 1, coherent light from laser 1 is reflected through galvanometric mirrors 2a, 2b and further reflected by dichroic mirror 3 to irradiate a specimen 5 through an objective 4, which also serves as a condenser lens. Since a laser is used as a light source, the irradiation takes place over a small area of the specimen. Since light from a laser is generally monochromatic in nature, it may have a wavelength corresponding to that of an exciting light. Those cases where monochromatic light is not obtained, an exciting filter 11 may be interposed as shown. Though the specimen is spotwise illuminated by the exciting light, a scanning in the X- and Y-directions over the specimen can be achieved by swinging the mirrors 2a, 2b in suitable directions. In response to such irradiation, the specimen produces fluorescence, which passes through the dichroic mirror 3. As is well recognized, the dichroic mirror 3 has a spectral response such that it reflects the exciting light but transmits the fluorescence. After passing through the dichroic mirror 3, the fluorescence produced by the cytoplasm (of a wavelength of 630 m$\mu$) is reflected by a dichroic mirror 6 while the fluorescence produced by the nucleus (of a wavelength of 530 m$\mu$) is transmitted therethrough. In this manner the respective components of the fluorescence are detected by a pair of light receiving elements 7a, 7b, which are in turn connected with amplifiers 8a, 8b, respectively. The outputs of these amplifiers are fed to an arithmetic unit 9, which performs a given calculation on the data input and feeds results to a display 10.

FIG. 2 shows the exciting light S which scans the cell in a direction indicated by an arrow $S_1$. The irradiated area of cell produces fluorescence condition due to the excitation. Since the wavelength of the fluorescence produced by the cytoplasm and that produced by the nucleus are different from each other as mentioned above, they can be separately detected by the light receiving elements and their total amount determined separately. The size is determined by the spacing between the point where the fluorescence is initially detected and the point where the fluorescence ceases to be produced, assuming that the scanning takes place in the manner illustrated in FIG. 2. By way of example, the fluorescence is produced by the cytoplasm when the exciting light S reaches the end $A_1$ of the cytoplasm A, so that the amount of light as detected by the element 7a increases gradually from zero, but reduces to zero again at the other end $A_2$, as shown in FIG. 3a. In a similar manner, the element 7b will detect the fluorescence when the exciting light S reaches the end $B_1$ of the nucleus B, and will reduce to zero when the point $B_2$ is reached, as shown in FIG. 3b. The lengths $L_1$, $L_2$ as measured a long the direction of travel of the scanning light between these ends may be determined. As shown, a filter 12a which transmits the light of a wavelength corresponding to the fluorescence emitted by the cytoplasm may be placed in front of the element 7a, and similarly another filter 12b which transmits the light of a wavelength corresponding to that of the fluorescence emitted by the nucleus may be placed in front of the element 7b. It is generally accepted that amount and the size of the cytoplasm does not vary significantly between benign and malignant cells while both the total amount and the size of the nucleus of a malignant cell are greater than those of a benign cell. This enables the determination of whether a cancer cell is present or not from the amount of fluorescence and from the size of the cytoplasm and the nucleus. It is also possible to determine whether or not a cell is affected by cancer, by examining the ratio of the size N of the nucleus to the size of the cytoplasm C, since the ratio is close to 1 for malignant cells. These determinations can be performed in the arithmetic unit 9 in an efficient and simple manner.

With the microscope of the invention, the scanning can be achieved with a spot beam of a small cross section but of a high brightness and the irradiation is possible with a highly monochromatic light. The speed of determination of the cell is increased inasmuch as the light of two different wavelengths are simultaneously measured to determine the total amount of light emitted by and the radius of the cytoplasm and the nucleus.

What is claimed is:

1. A microscope for scanning and determining the fluorescence of a cell comprised of a nucleus surrounded by cytoplasm, said microscope comprising:
   a laser light source for emitting light having a spot size smaller than the nucleus of the cell to be scanned;
   scanning means for directing the light from said light source onto the cell to spotwise irradiate the cell to produce fluorescence;
   means for splitting the produced fluorescence into components of different wavelengths; and
   detecting means for detecting the level of the fluorescence of the respective components.

2. The microscope of claim 1 wherein said scanning means includes a condenser lens interposed between said light source and the cell to be scanned for condensing the light emitted by said laser light source.

3. The microscope of claim 2 wherein said scanning means includes a pair of galvanometric mirrors interposed between said light source and the cell to be scanned for reflecting light emitted by said laser light source onto the cell to scan the cell in a spotwise manner.

4. The microscope of claim 1 wherein said splitting means comprises a dichroic mirror adapted to reflect light of a first wavelength and to transmit light of a second wavelength different from said first wavelength; and said detecting means comprises first and second light sensitive elements respectfully positioned to receive said reflected light and said transmitted light from said dichroic mirror for generating electrical signals representative of the levels of light of said first and second wavelengths.

5. The microscope of claim 4 further comprising means associated with said detecting means for determining the area of said cytoplasm and said nucleus whereby the ratios of two areas may be utilized to determine the presence of cancerous cells.

* * * * *